United States Patent [19]

Dieterich et al.

[11] 4,174,434

[45] Nov. 13, 1979

[54] COMPOUNDS CONTAINING HYDROXYL GROUPS AND URETHANO-ARYL-SULFONIC ACID GROUPS

[75] Inventors: Dieter Dieterich; Gerhard Balle, both of Leverkusen; Hans G. Schmelzer, Pulheim, all of Fed. Rep. of Germany

[73] Assignee: Bayer Aktiengesellschaft, Leverkusen, Fed. Rep. of Germany

[21] Appl. No.: 929,615

[22] Filed: Jul. 31, 1978

[30] Foreign Application Priority Data

Aug. 3, 1977 [DE]  Fed. Rep. of Germany ....... 2735013

[51] Int. Cl.² ............................................. C08L 81/00
[52] U.S. Cl. ...................................... 528/69; 528/71; 528/74; 528/76; 528/77; 528/80; 528/81; 528/83; 528/85; 560/10; 560/12; 560/13
[58] Field of Search ............... 560/10, 12, 13; 528/69, 528/71, 74, 76, 77, 80, 81, 83, 85

[56] References Cited

U.S. PATENT DOCUMENTS

| | | | |
|---|---|---|---|
| 3,826,769 | 7/1974 | Carlson | 260/29.2 TN |
| 4,119,658 | 10/1978 | Dieterich | 260/453 AR |

*Primary Examiner*—Maurice J. Welsh
*Attorney, Agent, or Firm*—Gene Harsh; Joseph C. Gil; R. Brent Olson

[57] ABSTRACT

The instant invention is directed to compounds having an average molecular weight of from 300 to 12,000, containing: at least one hydroxyl group and at least one urethano-aryl-sulfonic acid group and a method for their preparation. The process is characterized as a process for the preparation of compounds having a number average molecular weight of from 300 to 12,000 having at least one hydroxyl group and at least one urethano-aryl-sulfonic acid group, comprising: reacting at from 0° to 190° C.

(A) compounds having a molecular weight of from 62 to 10,000 having at least two hydroxyl groups; with (B) aromatic isocyanato sulfonic acids, wherein the equivalent ratio of the total quantity of isocyanate groups (including any isocyanate groups present in dimerized form) to sulfonic acid groups is from 0.5:1 to 50:1 and the equivalent ratio of the sum of hydroxyl groups in (A) to NCO groups is from 1.5:1 to 30:1. The invention is also directed to the product by the process.

10 Claims, No Drawings

COMPOUNDS CONTAINING HYDROXYL GROUPS AND URETHANO-ARYL-SULFONIC ACID GROUPS

BACKGROUND OF THE INVENTION

It is known to use compounds which contain from two to six OH groups and have a molecular weight of from 62 to about 10,000 for preparing polyurethanes. The following are examples of such polyhydroxyl compounds: simple polyhydric alcohols, e.g. ethylene glycol, diethylene glycol, hexane diol, glycerol, trimethylol propane. Further examples include higher molecular weight polyethers, polythioethers, polyesters and polyacetals. These higher molecular weight polyhydroxyl compounds are prepared from low molecular weight units in known manner. These hydroxyl compounds generally have only a low polarity and carry no other functional groups.

For preparing foams from polyisocyanates and polyhydroxyl compounds, it is generally necessary to use surface active compounds, especially organopolysiloxanes. These substances have an emulsifying action on the reactants and stabilize the foam structure which initially is still liquid. Emulsifiers are occasionally also used for the production of non-cellular polyurethanes if the reactants are insufficiently compatible or if fillers are used. In many cases, the emulsifier or stabilizer must be added as a separate component to the reaction mixture, which may entail problems of dosing because of the small quantities in which these components are generally used.

It would be advantageous if, for example, in the case of incompatibility of the reactants, it would be possible to dispense with the use of particular surface active compounds because the polyols used already have the desired surface active properties. There is therefore a need for polyols having surface active properties. Moreover, there is a demand for polyols which are hydrophilic and have a relatively high polarity so that they will have better compatibility with water and so that the foams produced from the polyols will have a certain water absorption capacity, as well as improved resistance to solvents. There is also a demand for polyhydroxyl compounds which yield polyurethanes having improved fire characteristics. Lastly, it would be desirable to have OH prepolymers available which do not give rise to toxic aromatic diamines when they undergo hydrolytic degradation.

The present invention provides a solution to these problems.

DESCRIPTION OF THE INVENTION

The instant invention is directed to a process wherein polyhydroxyl compounds are reacted with sub-equivalent molar quantities of aromatic isocyanatosulfonic acids, optionally in admixture with conventional polyisocyanates. The reaction products will be a mixture of hydroxyl containing compounds. These compounds have increased polarity and surface active properties and impart to the products produced from them improved fire characteristics, as well as the ability to be welded by high frequency welding. The instant invention is directed to the process, the mixture of compounds produced, specific compounds within the mixture, and the products by this specific process.

The present invention relates to compounds having an average molecular weight of from 300 to 12,000 which have at least one hydroxyl group and at least one urethane-arylsulfonic acid group.

Preferred compounds are those which have an average molecular weight of from 400 to 12,000 and are characterized by at least one OH-functional long chain containing from 15 to 400, preferably from 30 to 300, chain members. The chain members are, for example, $-CH(CH_3)-$ or $-CH_2-$groups, ether oxygen atoms, CO groups, sulfur atoms and/or nitrogen atoms.

The compounds according to the present invention preferably contain at least one structural unit corresponding to the following general formula:

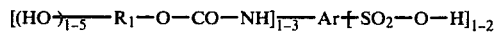

wherein
  $R_1$ represents the residue from a polyol containing from 2 to 6 OH groups e.g. a polyester, polyether, polythioether or polyester amide; and
  Ar represents a polyvalent group of an aromatic isocyanate.

Compounds corresponding to the following general formula are preferred according to the present invention:

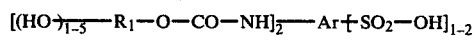

The present invention also relates to a process for the preparation of compounds having an average molecular weight of from 300 to 12,000 which have at least one hydroxyl group and at least one urethano-aryl-sulfonic acid group, characterized in that compounds having a molecular weight of from 62 to 10,000 which have at least two hydroxyl groups are reacted with aromatic isocyanato-sulfonic acids at from 0° to 190° C., using an equivalent ratio of the total quantity of isocyanate groups (including any isocyanate groups present in dimerized form) to sulfonic acid groups of from 0.5:1 to 50:1 and an equivalent ratio of hydroxyl groups to isocyanate groups of from 1.5:1 to 30:1.

Furthermore, the present invention relates to the use of the compounds according to the present invention as reactants for polyisocyanates for the production of polyaddition products or polycondensation products.

Compared with the known polyhydroxyl compounds, the new compounds according to the present invention have numerous advantageous properties, as indicated below:

1. They have a highly polar or surface active character and an exceptionally low vapor pressure and they have excellent compatibility with numerous polar and apolar media and reactants.

2. Both the surface active properties and the hydrophilic character may be controlled within wide limits as desired according to the nature and quantity of the isocyanato-arylsulfonic acid used in the process and the nature and quantity of the bases used for neutralizing the sulfonic acid groups.

3. Hydrolytic degradation of the products results in toxicologically harmless amino sulfonic acids.

4. The use of the compounds according to the present invention, for example for the production of polyurethanes, results in products which have improved fire characteristics. When carrying out the process according to the present invention, part of the OH groups of the polyhydroxyl compounds used as starting material undergo addition with the isocyanate groups and any uretdione groups optionally present in the isocyanatoaryl sulfonic acid to form higher molecular weight new polyhydroxyl compounds which, at least in part, contain urethane groups and one or more free sulfonic acid groups. The sulfonic acid groups may subsequently be partly or completely neutralized with conventional inorganic or organic bases.

Any of the compounds conventionally used in polyurethane chemistry which have a molecular weight of from 62 to 10,000 and contain at least two hydroxyl groups may be used as starting material for the process according to the present invention. The following are examples: low molecular weight glycols, polyesters, polyethers, polyester amides, OH-functional oligomers, polymers, for example polyethers based on butadiene or grafted with vinyl monomers or also polyethers which contain other polymers, such as polyureas, urea resins, polyhydrazodicarbonamides or vinyl polymers dispersed in them. Examples of suitable hydroxy-functional compounds are given below.

Suitable polyesters containing hydroxyl groups include, e.g. reaction products of polyhydric, preferably dihydric, alcohols, optionally with the addition of trihydric alcohols, and polybasic, preferable dibasic, carboxylic acids. Instead of free polycarboxylic acids, the corresponding polycarboxylic acid anhydrides or corresponding polycarboxylic acid esters of lower alcohols or mixtures thereof may be used for preparing the polyesters. The polycarboxylic acids may be aliphatic, cycloaliphatic, aromatic and/or heterocyclic. They may be substituted, e.g. by halogen atoms, and/or they may be unsaturated. The following are suitable examples: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids, such as oleic acid, optionally mixed with monomeric fatty acids, dimethyl terephthalate and terephthalic acid-bis-glycol esters. The following are examples of suitable polyhydric alcohols: ethylene glycol, propylene glycol-(1,2) and -(1,3), butylene glycol-(1,4) and -(2,3), hexanediol-(1,6), octanediol-(1,8), neopentylglycol, cyclohexanedimethanol, (1,4-bis-hydroxymethylcyclohexane), 2-methyl-1,3 propanediol, glycerol, trimethylolpropane, hexanetriol-(1,2,6), butanetriol-(1,2,4), trimethylolethane, pentaerythritol, quinitol, mannitol, sorbitol, methylglycoside, diethylene glycol, triethylene glycol, tetraethylene glycol, polyethylene glycols, dipropylene glycol, polypropylene glycols, dibutylene glycol and polybutylene glycols. The polyesters may also contain a proportion of carboxyl end groups. Polyesters of lactones, such as ε-caprolactone, or hydroxycarboxylic acids, such as ω-hydroxycaproic acid, may also be used.

The polyethers of the invention, which preferably have two hydroxyl groups, are also known and are prepared, for example, by polymerization of epoxides, such as ethylene oxide, propylene oxide, butylene oxide, tetrahydrofuran, styrene oxide or epichlorohydrin or 1.1.1-trichloroacetene-3,4-oxide. They may be polymerized on their own, e.g. in the presence of $BF_3$, or by addition of these epoxides, if desired, as mixtures or successively, to starting components having reactive hydrogen atoms. Examples of starting components include alcohols such as ethylene glycol, propylene glycol-(1,3) or -(1,2), or 4,4'-dihydroxydiphenylpropane, amines such as aniline or water.

Polyethers modified by vinyl polymers, for example the compounds obtained by the polymerization of styrene or acrylonitrile in the presence of polyethers (U.S. Pat. Nos. 3,383,351; 3,304,273; 3,523,093; and 3,110,695 and German Pat. No. 1,152,536) are also suitable. The higher functional polyethers which may also be included in limited amounts are obtained analogously by the known method of alkoxylation of higher functional starter molecules, such as ammonia, ethanolamine, ethylene diamine or sucrose.

Preferred polythioethers are the condensation products obtained by reacting thiodiglycol on its own and/or with other glycols, dicarboxylic acids, formaldehyde, aminocarboxylic acids or amino alcohols. The products obtained are polythio mixed ethers, polythio ether esters or polythio ether ester amides, depending on the co-components.

Suitable polyacetals include, for example, the compounds which may be prepared by the reaction of glycols, such as diethylene glycol, triethylene glycol, 4,4'-dioxethoxydiphenyl dimethylmethane and hexanediol, with formaldehyde. Suitable polyacetals for the purposes of the present invention may also be prepared by the polymerization of cyclic acetals.

The polycarbonates containing hydroxyl groups used may be of the type which may be prepared by the reaction of diols, such as propanediol-(1,3), butanediol-(1,4) and/or hexanediol-(1,6), diethylene glycol, triethylene glycol or tetraethylene glycol, with diaryl carbonates, e.g. diphenyl carbonate, or with phosgene.

Suitable polyester amides and polyamides include, for example, the predominantly linear condensates prepared from poly-basic saturated and unsaturated carboxylic acids or the anhydrides thereof and polyfunctional saturated and unsaturated amino alcohols, diamines, polyamines and mixtures thereof. Polyhydroxyl compounds which already contain urethane or urea groups may also be used.

There may also be used polyhydroxyl compounds which contain high molecular weight polyadducts or polycondensates in a finely dispersed or dissolved form. Such modified polyhydroxyl compounds are obtained when polyaddition reactions (e.g. reactions between polyisocyanates and amino-functional compounds) or polycondensation reactions (e.g. between formaldehyde and phenols and/or amines) are carried out in situ in the above-mentioned hydroxyl group-containing compounds. Processes of this type have been described in German Auslegeschriften Nos. 1,168,075 and 1,260,142 and in German Offenlegungsschriften Nos. 2,324,134; 2,423,984; 2,512,385; 2,513,815; 2,550,796; 2,550,797; 2,550,833; and 2,550,662. Such modified polyhydroxyl compounds may also be obtained according to U.S. Pat. No. 3,869,413 or German Offenlegungsschrift No. 2,550,860 by mixing a previously prepared aqueous polymer dispersion with a polyhydroxyl compound and then removing the water from the mixture.

The following are examples of low molecular weight glycols which may be reacted with isocyanatosulfonic acids, either on their own or as mixtures with the above-mentioned higher molecular weight polyhydroxyl compounds: ethylene glycol, diethylene glycol, triethylene glycol, tetraethylene glycol, propylene glycol, oligopropylene glycols, propylene glycol-(1,3), butanediol hexanediol, 2-ethyl-hexanediol, octanediol, glycerol, trimethylol-propane and dodecanediol. Amino-alcohols, such as ethanolamine, propanolamine or diethanolamine, may also be used, provided all the amino groups present are reacted with isocyanate groups. Mono-, di- or poly-amines or water may also be used in minor quantities. The products obtained from the reaction should at the most contain only minor quantities of carboxyl groups or mercapto groups in addition to the OH groups.

The isocyanato-aryl-sulfonic acids used in the process according to the present invention may be sulfonation products of any known aromatic polyisocyanates. The following are examples of such aromatic polyisocyanates which may be used in the form of the sulfonatin products thereof in the process:

4,4'-stilbene-diisocyanate; 4,4'-dibenzyl-diisocyanate; 3,3'- and 2,2'-dimethyl-4,4'-diisocyanatodiphenylmethane; 2,3,2',5'-tetramethyl-4,4'-diisocyanatodiphenylmethane; 3,3'-dimethoxy-4,4'-diisocyanatodiphenylmethane; 3,3'-dichloro-4,4'-diisocyanato-diphenylmethane; 4,4'-diisocyanatodiphenyl-cyclohexylmethane; 4,4'-diisocyanato-benzophenone; 4,4'-diisocyanatodiphenyl-sulphone; 4,4'-diisocyanatodiphenyl ether; 4,4'-diisocyanato-3,3'-dibromodiphenylmethane; 4,4-diisocyanato-3,3'-diethyldiphenylmethane; 4,4'-diisocyanatodiphenylethylene-(1,2); 4,4'-diisocyanatodiphenylsulphide; 1,3- and 1,4-phenylene-diisocyanate; 2,4- and 2,6-tolylene diisocyanate and mixtures of these isomers; diphenylmethane-2,4'- and/or -4,4'-diisocyanate; naphthylene-1,5-diisocyanate; triphenylmethane-4,4',4''-triisocyanate; polyphenyl-polymethylene polyisocyanates of the type obtained by aniline formaldehyde condensation followed by phosgenation, which have been described, for example, in British Pat. Nos. 874,430 and 848,671; polyisocyanates having carbodiimide groups as described in German Pat. No. 1,092,007; diisocyanates of the type described in U.S. Pat. No. 3,492,330, polyisocyanates having allophanate groups as described, e.g. in British Pat. No. 994,890, Belgian Pat. No. 761,626 and published Dutch patent application No. 7,102,524; polyisocyanates having isocyanurate groups as described, e.g. in German Pat. Nos. 1,022,789; 1,222,067 and 1,027,394 and in German Offenlegungsschriften Nos. 1,929,034 and 2,004,048; polyisocyanates having acylated urea groups, according to German Pat. No. 1,230,778; polyisocyanates having biuret groups, e.g. as described in German Pat. No. 1,101,394, British Pat. No. 889,050 and French Pat. No. 7,017,514. The distillation residues obtained from the commercial production of isocyanates and still containing isocyanate groups may also be used, optionally as solutions in one or more of the above-mentioned polyisocyanates. Mixtures of the above-mentioned polyisocyanates may also be used.

Phosgenation products of condensates of aniline with aldehydes or ketones, such as acetaldehyde, propionaldehyde, butyraldehyde, acetone or methylethyl ketone, are also suitable. The phosgenation products of condensates of aniline which are alkyl-substituted on the nucleus, such as toluidines, with aldehydes or ketones, such as formaldehyde, acetaldehyde, butyraldehyde, acetone or methylethyl ketone, are also suitable.

Reaction products of the above-mentioned aromatic polyisocyanate mixtures with from 0.2 to 50 mol% of polyols are also suitable, provided the viscosity of the resulting reaction products does not exceed 50,000 cP at 25° C. and the isocyanate content of the reaction products is at least 6%, by weight. Suitable polyols for the modification of the starting materials include, in particular, polyether- and polyester- polyols with a molecular weight of from 200 to 6,000, preferably from 300 to 4,000, which are known in polyurethane chemistry, and low molecular weight polyols with a molecular weight of from 62 to 200 are also suitable. Examples of such low molecular weight polyols include ethylene glycol, propylene glycol, glycerol, trimethylol propane and 1,4,6-hexanetriol.

Particularly preferred isocyanatoaryl-sulfonic acids are the sulfonation products of tolylene-2,4-diisocyanate and mixtures of tolylene-2,4- and -2,6-diisocyanate. Likewise preferred are the sulfonation products of di- or poly-isocyanates obtained by the phosgenation of aniline/formaldehyde condensates and the products of partial sulfonation of aromatic polyisocyanates. The products of partial sulfonation of chemically uniform diisocyanates or of binary isomeric mixtures are generally obtained as suspensions whereas the partial sulfonation of multi-component mixtures generally results in homogeneous solutions. For the process of the present invention, it is immaterial in principle whether solutions or suspensions are used. Partially sulfonated polyisocyanate mixtures of the type which are obtained by the phosgenation of aniline/formaldehyde condensates and which have been described in German Offenlegungsschriften Nos. 2,227,111; 2,359,614 and 2,359,615 are particularly suitable. Suspensions of diisocyanatotoluene-sulfonic acid dimers and diisocyanatodiphenylmethane-sulfonic acid dimers in diisocyanatotoluene or diisocyanato-diphenylmethane are also particularly preferred.

The preparation of isocyanatoaryl-sulfonic acids used in the process, or mixtures thereof with unsulfonated aromatic polyisocyanates, is carried out by processes known in the art or by analogous processes such as those based on the processes disclosed in the above-mentioned publications or in U.S. Pat. No. 3,826,769. The processes according to German Offenlegungsschriften 25 24 476 and 26 15 876 are also suitable for the preparation of isocyanatoaryl sulfonic acids which may be used in the process according to the present invention.

Solutions or suspensions of the exemplified isocyanatoaryl sulfonic acids in aliphatic polyisocyanates, such as tetramethylene diisocyanate or hexamethylene diisocyanate, and/or in cycloaliphatic or mixed aliphatic-cycloaliphatic polyisocyanates, such as 4,4'-diisocyanatodicyclohexylmethane, 2,4- or 2,6-diisocyanato-hexahydrotoluene or 1-isocyanato-3,3,5-trimethyl-5-isocyanatomethylcyclohexane, may also be used in the process. If it is desired to lower the isocyanate functionality of the products obtained by the process of the invention, there may also be used solutions or suspensions of the isocyanatoaryl-sulfonic acids in aromatic, aliphatic or cycloaliphatic monoisocyanates. Examples of suitable monoisocyanates include phenylisocyanate, tosylisocyanate, n-hexylisocyanate, 6-chlorohexylisocyanate, cyclohexylisocyanate and methoxymethylisocyanate. It would also be possible to use sulfonated aromatic monoisocyanates, such as phenylisocyanate, as the isocyanatoaryl-sulfonic acid in combination with unsulfonated polyisocyanates of the type exemplified. The nature and proportions of the isocyanates to be used in the process of the invention and the degree of sulfonation are frequently chosen so that the equivalent ratio of isocyanate groups which may be partially present in dimerized form, to sulfonic acid groups is greater than 1:1, i.e. in particular from 1.05:1 to 50:1, preferably from 2:1 to 30:1. A ratio of from 2:1 to 12:1 is particularly preferred.

Another group of preferred isocyanato sulfonic acids consists of those aromatic mono-, di- or poly-isocyanates which contain more than one sulfonic acid group and in particular two or three sulfonic acid groups. Isocyanatopolysulfonic acids of this type have been described in German Offenlegungsschrift No. 2,615,876. If monocyanato-disulfonic acids are used as part or all of the sulfonic acid component, the equivalent ratio of NCO groups to SO$_3$H groups may also be from 1:1 to 0.5:1.

For the preparation of hydroxyl compounds which have sulfonic acid or sulfonate groups in end positions, it is preferred to use monoisocyanato-sulfonic acids, e.g. the sulfonation products of phenylisocyanate, m-tolylisocyanate, p-tolylisocyanate, p-chlorophenylisocyanate, p-nitrophenylisocyanate, p-methoxyphenylisocyanate, p-chloromethyl-phenylisocyanate, m-chlorophenylisocyanate and m-chloromethylphenylisocyanate.

The ratio of polyhydroxyl compounds to isocyanato-sulfonic acid is in most cases chosen so that OH-functional products having a molecular weight below 12,000, preferably below 6,000, are produced. This means that a molar excess of hydroxy-functional components are used, amounting to at least 1.5 OH groups per NCO group. By "NCO groups" are meant not only free NCO groups but also dimerized NCO groups in the form of uretdione groups. The hydroxy-functional compounds used as starting materials are most preferably modified only partly with sulfonic acid groups, in which case up to 30 OH groups may be used per NCO group. An equivalent ratio of OH groups to NCO groups of from 2:1 to 20:1 is preferred.

The above-mentioned proportions apply mainly to reactons which are carried out using di- or poly-isocyanates and which lead directly to polyhydroxyl compounds which are modified with sulfonic acid groups.

However, monoisocyanates containing from 1 to 3 sulfonic acid groups may also be used for the present invention. These monoisocyanates are reacted in subequivalent molar quantities with the hydroxyl compounds used as starting materials.

The equivalent ratio of OH groups to NCO groups is preferably from 2 to 6.

The method employed for reacting the hydroxyl compounds used as starting materials with isocyanates which contain sulfonic acid groups is known in principle. Generally, the hydroxyl compounds are first introduced into the reaction vessel and the isocyanate component is added under conditions of mixing. If the isocyanate is liquid, as, for example, in the case of partially sulfonated MDI types, mixing of the components and the subsequent reaction may easily be carried out at room temperature or slightly elevated temperatures. The choice of temperature in this case depends entirely on the viscosity of the reaction mixture and the desired reaction time. If solid isocyanatoaryl mono- or poly-sulfonic acids are used, a suspension is first formed when the reactants are mixed, and it is advisable to carry out the reaction at a temperature at which the solid isocyanate rapidly goes into solution.

Temperatures of from 40° to 180° C., particularly from 60° to 120° C., are suitable for this purpose. Temperatures above 120° C., up to about 200° C., are preferred in particular when relatively low molecular weight polyhydroxyl compounds are used exclusively, in order to prevent solidification of the reaction mixture during the reaction. Solid isocyanato-sulfonic acids are preferably used in the form of suspensions, pastes or moist powders, using inert solvents as described in German Offenlegungsschrift No. 2,640,103.

Solid isocyanato-sulfonic acids may also be used in the form of solutions in organic solvents, preferably using liquid esters of an inorganic or organic acid of phosphorus as solvent (German Offenlegungsschrift No. 2,650,172).

Any inert solvents, such as hydrocarbons, halogenated hydrocarbons, ethers, or ketones may be added to the reaction mixture. However, it is preferred to carry out the reaction in the absence of solvents or with only the small quantities of solvent required for dissolving solid isocyanato-sulfonic acids or converting them into pastes.

According to a preferred embodiment of the process, asymmetric hydroxyl compounds are prepared by making use of the differing reactivities of the isocyanate groups. For example, a diisocyanatoaryl-sulfonic acid may first be reacted with a monofunctional alcohol, a fatty acid, an amino alcohol or a primary or secondary amine, e.g. up to from 20 to 70% conversion. Then the remaining isocyanate groups may be reacted with a di- or polyhydroxyl compound. The surface active properties may be widely varied according to the nature and quantity of the monofunctional component, as well as of the polyfunctional component.

Monofunctional compounds which may be used in addition to the above-mentioned polyhydroxyl compounds include, for example, methanol, ethanol, isopropanol, n-butanol, glycolmonomethyl ether, glycolmonoethyl ether, diglycolmonomethyl ether, n-octanol, n-dodecanol, oleyl alcohol, stearyl alcohol, hydroxy-functional fatty acid esters of glycerol, trimethylolpropane, trimethylolethane, stearic acid, coconut fatty acid, linseed oil fatty acid, soya-bean oil fatty acid, aminoethanol, aminopropanol (amino alcohols of this type may be regarded as approximately mono-functional for the purpose of the procedure described above on account of the wide difference in reactivity between the amino function and the hydroxyl function), butylamine, secondary butylamine and coconut fatty amine.

The stepwise preparation of such asymmetric hydroxyl compounds is most preferably carried out in a solvent, e.g. in acetone or an organic phosphoric acid ester. Short-chain hydrophilic monofunctional compounds are preferably combined with predominantly hydrophobic polyhydroxyl compounds, whereas long-chain hydrophobic monofunctional compounds are preferably combined with hydrophilic polyhydroxyl compounds.

The hydroxyl compounds containing sulfonic acid groups may be partly or completely neutralized using organic or inorganic bases. Suitable neutralizing agents are, e.g. organic bases, such as monofunctional primary, secondary and tertiary amines. Examples are methylamine, diethylamine, triethylamine, trimethylamine, dimethylamine, ethylamine, tributylamine, pyridine, aniline, toluidine, alkoxylated amines, such as ethanolamine, diethanolamine, triethanolamine, methyldiethanolamine, dimethylaminoethanol or oleyldiethanolamine. Other neutralizing agents are polyfunctional polyamines in which the individual amino groups may differ in the basicity thereof, e.g. the polyamines obtained by the hydrogenation of addition products of acrylonitrile with primary and secondary amines, per alkylated or partially alkylated polyamines, such as N,N-dimethylethylene diamine, or compounds, such as α-aminopyridine or N,N-dimethylhydrazine. Inorganic bases, compounds which are basic in reaction or split off bases, such as ammonia or monovalent metal hydroxydes, carbonates or oxides, such as sodium hydroxide or potassium hydroxide may also be used.

Suitable neutralizing agents also include guanidines, guanidine carbonate, urea, methyl urea, dimethyl urea, caprolactam, dimethylformamide, dimethylacetamide, pyrrolidone and solid inorganic bases. Examples of solid inorganic bases are calcium oxide, calcium hydroxide, calcium carbonate, magnesium oxide, magnesium carbonate, dolomite, lithium hydroxide, lithium carbonate, zinc oxide, zinc carbonate and basic inorganic fillers.

Weak basic neutralizing agents, such as urea or caprolactam, and basic fillers may be used in excess over the sulfonic acid groups present.

The products of the present invention are valuable starting materials for the production of polyurethane plastics by the isocyanate polyaddition process. They are suitable, for example, for the production of non-cellular or cellular elastomers, flexible foams and rigid foams, especially where high demands are made on the cross-linking density, fire characteristics or degradability. Thus, for example, the polyhydroxyl compounds of the invention are suitable for the manufacture of upholstery padding, mattresses, elastic underlays, motor car seats, damping materials, shock absorbers, constructional materials, sound damping insulations and moisture absorbing materials, e.g. for the surgical field, and for the manufacture of substrates for cultivating plants, and for protection against heat and cold. The polyhydroxyl compounds are particularly suitable for the production of inorganic-organic synthetic materials, for example by processes analogous to those described in German Pat. No. 2,310,559 and German Offenlegungsschriften Nos. 2,227,147 and 2,359,608, and for the production of surface coatings, impregnations and bonds.

The products are versatile in their use. They can be used as surface active compounds, e.g. as emulsifiers or foam stabilizers, and as dye auxiliaries or flotation substances and for the preparation of polyurethane dispersions.

One particular advantage of the hydroxyl compounds of the invention is their increased polarity. This distinguishes the products, for example from pure polypropylene glycol ethers, in rendering them compatible with low molecular weight glycols, such as ethylene glycol, diethylene glycol, 1,4-butanediol or glycerol. Mixtures are homogeneous and therefore stable in storage.

The reaction of the polyhydroxyl compounds of the invention with polyisocyanates which contain sulfonic acid ester groups is particularly suitable for the preparation of polyaddition products which have good fire characteristics.

The compounds of the invention are particularly to be recommended when polyisocyanate components and polyhydroxyl components, due to the incompatibility thereof, first form emulsions which must subsequently be rendered homogeneous after a certain period of induction. Even very small quantities of the products promote the formation of exceptionally finely divided emulsions which react much more rapidly. Moreover, the new products influence the pore structure of foams produced from them and in many cases effect a desirable increase in the compression resistance. Lastly, the products are also suitable for rendering surface-modified inorganic fillers hydrophobic.

EXAMPLE 1

2,000 g of a polypropylene ether having an OH number of 42 and started on 84% of trimethylol propane and 16% of 1,2-propylene glycol are intimately mixed at room temperature with 62 g of the toluene-moist uretdione of diisocyanatotoluene sulfonic acid (prepared from tolylene diisocyanate, isomeric mixture 2,4:2,6=80:20), corresponding to 40 g of dry substance. The suspension is heated to 110° C. within 45 minutes and maintained at from 100° to 125° C. for 3 hours. Toluene is evaporated off at 14 Torr and 100° C. and the solution is filtered.

Sulfur content: 0.24%;
Viscosity: 2,200 cP;
pH of a solution of 1 g of product in 90 g of methanol and 10 g of water: 2.7.

EXAMPLE 2

38 g of a 15% methanolic potassium hydroxide solution are added to 1021 g of the product from Example 1 and the methanol is evaporated off under vacuum at 35° C.

pH: 8;
Viscosity: 1700 cP.

EXAMPLE 3

The procedure is the same as in Example 1, but using 154 g (100 g of dry substance) of uretdione.
Viscosity: 32,000 cP.

EXAMPLE 4

83 g of a 15% methanolic potassium hydroxide solution are added to 1064 g of the product from Example 3 and the methanol is evaporated off under vacuum at 35° C.

pH: 8;
Viscosity: 90,000 cP.

EXAMPLE 5

4,000 g of a polypropylene polyether which has been started on trimethylol propane and contains 13% of ethylene glycol ether groups in end positions and has an OH number of 35 are intimately mixed at room temperature with 123 g (80 g of dry substance) of the uretdione described in Example 1. The reaction mixture is stirred at from 25° to 27° C. under nitrogen for 1 hour, then heated to 50° C. and maintained at this temperature for 4 hours, during which time the toluene is evaporated off by application of a water jet vacuum. Most of the uretdione goes into solution. Stirring is then continued for 8 hours at from 60° to 65° C. and the solution is filtered. Ca. 0.3 g of residue are left on the filter.

OH number: 36.4;
Acid number: 4.7.

EXAMPLE 6

77 g of a 15% methanolic potassium hydroxide solution are added to 2060 g of the product from Example 5 and the methanol is evaporated off under vacuum at 35° C.

pH: 8;
OH number: 32.6
Acid number: 0.2.

EXAMPLE 7

The procedure is the same as in Example 5, but starting from a corresponding polyether of OH number 28. A yellowish-brown, viscous modified polyether is obtained.
OH number: 28.1;
Acid number: 4.7.

EXAMPLE 8

69 g of a 15% methanolic potassium hydroxide solution are added to 2060 g of the product from Example 7 and the methanol is evaporated off under vacuum at 35° C.
pH: 7.5;
OH number: 21.4;
Acid number: 0.2.

EXAMPLE 9

200 g of the uretdione of diisocyanatotoluene sulfonic acid (see Example 1) are triturated with 373 g of toluene and mixed, with stirring at 50° C. with 10 kg of a polypropylene ether which has been started on trimethylol propane and contains 17% of ethylene glycol ether groups as end groups and has an OH number of 35. The temperature is then raised to 60° C. and the toluene is evaporated off by application of a water jet vacuum. The uretdione dissolves virtually quantitatively within 9 hours. The modified polyether is finally filtered over a fine metal sieve at 60° C.
OH number: 34.5;
Acid number: 4.3;
Sulfur content: 0.2%.

If the uretdione is triturated with 200 g of trischloroethyl phosphate instead of with toluene before it is added to the polyether, the product goes into solution after a short time at 60° C.

EXAMPLE 10

380 g of toluene-moist uretdione of diisocyanatotoluene sulfonic acid (see Example 1) corresponding to 300 g of dry substance are thoroughly triturated with 550 g of toluene and added with stirring at 50° C. to 15 kg of a polypropylene ether which has been started on trimethylol propane, contains 13% of ethylene glycol ether groups in end positions and has an OH number of 28. The reaction mixture is then heated to 65° C. and stirred for 5 hours, during which time most of the uretdione goes into solution. During a further 3 hours stirring at 65° C., the toluene is distilled off in a water jet vacuum and the product obtained is filtered over a metal sieve at 50° C. to remove ca. 4 g of undissolved constituents.
OH number: 22.2;
Acid number: 4.7;
Sulfur content: 0.22%
Toluene content: 0.6%.

EXAMPLE 11

156 g of a 15% methanolic potassium hydroxide solution are added dropwise with stirring at room temperature over a period of 1 hour to 5000 g of the product obtained according to Example 10. The methanol is then distilled off in a water jet vacuum at temperatures of up to 55° C. The resulting sulfonate group-containing polyether has a viscosity of 3,400 cP.
OH number: 21.2;
Acid number: 0.9.

EXAMPLE 12

42 g of triethylamine are added dropwise at room temperature within 2 hours to 5000 g of the polyether obtained according to Example 10. Stirring is then continued for a further 5 hours at room temperature.
Viscosity: 3,400 cP;
OH number: 23.9.

EXAMPLE 13

142 g of bis-(2-hydroxyethyl)-oleylamine are added dropwise to 4,800 g of the polyether obtained according to Example 10. The reaction mixture is then stirred for 4 hours at room temperature.
Viscosity: 3,800 cP;
OH number: 34.4.

The following materials were used for the foaming experiments:

Polyol A: polyoxyalkylene ether triol having an equivalent weight of 2000, containing polyoxyethylene blocks in end positions and containing over 80% of primary hydroxyl groups.
Polyol B: the sulfonic acid group-containing polyether-polyol from Example 8, neutralized with KOH.
Polyol C: the sulfonic acid group-containing polyether-polyol from Example 11, neutralized with KOH.
Polyol D: corresponds to polyol C, but neutralized with triethylamine (Example 12).
Polyol E: corresponds to polyol C, but neutralized with N,N-dihydroxy-ethyloleylamine (Example 13).
Dabco: 1,4-diazabicyclo octane (triethylene diamine).
TCAP: tris-(2-chloroethy)-phosphate.

EXAMPLE 14

The following components were weighed into a cardboard cup and vigorously stirred using a high-speed stirrer for 60 seconds:
100 parts, by weight, of polyol A
100 parts, by weight, of polyol B
6.4 parts, by weight, of water
0.2 parts, by weight, of "Dabco"
7.2 parts, by weight, of diisopropanolamine
2.0 parts, by weight, of triethanolamine
2.0 parts, by weight, of diethanolamine
4.0 parts, by weight, of TCAP
1.0 part, by weight, of a short-chain polyphenylsiloxane stabilizer according to German Offenlegungsschrift No. 2,232,525.

55.4 Parts, by weight, (corresponding to an NCO-/OH index=100) of a modified tolylene diisocyanate (Desmodur MT 58, allophanate-TDI) were added to the homogeneous mixture and rapidly mixed in. The mixture began to foam after 5 seconds. It was immediately poured into a rectangular mold formed by folding paper and it foamed within 60 seconds and had set 10 seconds after foaming ended. A highly elastic foam having a fine cell structure, a unit weight of 36 g/l and high compression resistance and tensile strength was obtained. A strip of the foam 2 cm in thickness and 10 cm in width was exposed at one end to the blue flame of a Bunsen burner. The foam burned with a small amount of smoke and melted slightly, but extinguished itself shortly after removal of the Bunsen flame.

EXAMPLES 15 TO 17

Foams were produced from the following formulations (quantities in parts, by weight) by the methods described in Example 14:

|  | 15 | 16 | 17 |
|---|---|---|---|
| Polyol C | 100 | — | — |
| Polyol D | — | 100 | — |
| Polyol E | — | — | 100 |
| Water | 3.2 | 3.2 | 3.2 |
| Dabco | 0.2 | 0.2 | 0.2 |
| Diisopropanolamine | 3.6 | 3.6 | 3.6 |
| Triethanolamine | 1.0 | 1.0 | 1.0 |
| Diethanolamine | 1.0 | 1.0 | 1.0 |
| TCAP | 2.0 | 2.0 | 2.0 |
| Polyphenylsiloxane as in Example 1 | 3.0 | 3.5 | 3.0 |
| Bis-2-N,N-dimethyl-aminoethyl ether | 0.2 | 0.2 | 0.25 |
| Modified tolylene diisocyanate (according to example 14) | 55.2 | 55.2 | 55.2 |
| NCO/OH index | 100 | 100 | 100 |

The following reaction times were found during foaming:

|  | a | b | c |
|---|---|---|---|
| Stirring time (cream time) | 10" | 6" | 6" |
| Rise time | 90" | 80" | 90" |
| Gel time | 25" | 20" | 20" |

The foams obtained correspond generally to the mechanical properties and fire characteristics to the foam from Example 14.

COMPARISON EXAMPLE

For comparison, a foam was produced from the same formulation, but using polyol A alone.

| Polyol A | 100 parts, by weight |
|---|---|
| Water | 3.2 parts, by weight |
| Dabco | 0.1 part, by weight |
| Diisopropanolamine | 3.6 parts, by weight |
| Triethanolamine | 1.0 part, by weight |
| Diethanolamine | 1.0 part, by weight |
| TCAP | 2.0 parts, by weight |
| Polyphenylsiloxane as in Example 1 | 1.0 part, by weight |
| Modified tolylene diisocyanate | 56.3 parts, by weight |
| NCO/OH index | 100 |

The following reaction times were found:

| Stirring time | 15" |
|---|---|
| Rise Time | 240" |
| Gel time | 165" |

The comparison foam requires considerably longer periods for rising and hardening than the foams described in the Examples. The surface also remains tacky for considerably longer.

What is claimed is:

1. Compounds having an average molecular weight of from 300 to 12,000, containing: at least one hydroxyl group and at least one urethano-aryl-sulfonic acid group.

2. The compounds of claim 1, further comprising at least one hydroxyl functional long chain containing from 15 to 400 chain members selected from the group consisting of —CH(CH$_3$) groups, CH$_2$ groups, ether oxygen atoms, CO groups, sulfur atoms, nitrogen atoms, or mixtures thereof and wherein the molecular weight is from 400 to 12,000.

3. The compounds of claim 2, wherein said at least one hydroxyl functional long chain contains from 30 to 300 chain members selected from the group consisting of —CH(CH$_3$) groups, CH$_2$ groups, ether oxygen atoms, CO groups, sulfur atoms, nitrogen atoms, or mixtures thereof.

4. Compounds having an average molecular weight of from 300 to 12,000 comprising a hydroxyl group and a urethane-aryl-sulfonic acid group prepared by reacting at from 0° to 190° C.

(A) compounds having a molecular weight of from 62 to 10,000 having at least two hydroxyl groups; with (B) aromatic isocyanato sulfonic acids, wherein the equivalent ratio of the total quantity of isocyanate groups (including any isocyanate groups present in dimerized form) to sulfonic acid groups is from 0.5:1 to 50:1 and the equivalent ratio of the sum of hydroxyl groups in (A) to isocyanate groups is from 1:5:1 to 30:1.

5. The compounds of claim 4 having an average molecular weight of from 400 to 12,000, further comprising: a hydroxyl functional long-chain containing from 15 to 400 chain members selected from the group consisting of —CH(CH$_3$) groups, CH$_2$ groups, ether oxygen atoms, CO groups, sulfur atoms, nitrogen atoms, or mixtures thereof.

6. The compounds of claim 5 wherein said OH-functional long-chain contains from 30 to 300 chain members selected from the group consisting of —CH(CH$_3$) groups, CH$_2$ groups, ether oxygen atoms, CO groups, sulfur atoms, nitrogen atoms, or mixtures thereof.

7. The compounds of claim 4 corresponding to the formula:

wherein
R represents the residue from a polyol containing from 2 to 6 OH groups;
Ar represents a polyvalent group of an aromatic isocyanate; and
n represents an integer from 1 to 3.

8. The compounds of claim 7, wherein n is 2.

9. A process for the preparation of compounds having a number average molecular weight of from 300 to 12,000 having at least one hydroxyl group and at least one urethano-arylsulfonic acid group, comprising: reacting at from 0° to 190° C.

(A) compounds having a molecular weight of from 62 to 10,000 having at least two hydroxyl groups; with (B) aromatic isocyanato sulfonic acids, wherein the equivalent ratio of the total quantity of isocyanate groups (including any isocyanate groups present in dimerized form) to sulfonic acid groups is from 0.5:1 to 50:1 and the equivalent ratio of the sum of hydroxyl groups in (A) to NCO groups is from 1.5:1 to 30:1.

10. The process of claim 9, wherein component (B) is selected from the group consisting of the sulfonation products of tolylene-2,4-diisocyanate, tolylene-2,6-diisocyanate, and mixtures thereof.

* * * * *